United States Patent [19]

May et al.

[11] Patent Number: 4,913,882
[45] Date of Patent: Apr. 3, 1990

[54] DIFFUSION SAMPLER HAVING A CONVERSION ZONE

[75] Inventors: Wolfgang May, Reinfeld; Edgar Eickeler; Wolfgang Evers, both of Lübeck, all of Fed. Rep. of Germany

[73] Assignee: Drägerwerk Aktiengesellschaft, Lübeck, Fed. Rep. of Germany

[21] Appl. No.: 239,469

[22] Filed: Sep. 1, 1988

[30] Foreign Application Priority Data

Sep. 1, 1987 [DE] Fed. Rep. of Germany ....... 3729080

[51] Int. Cl.⁴ .................... G01N 31/22; G01N 21/75
[52] U.S. Cl. .......................................... 422/58; 422/83; 422/86; 422/88; 422/101; 436/116; 436/167; 436/178; 436/902; 73/863.23
[58] Field of Search .............. 422/58, 61, 83, 86, 422/87, 88, 101; 73/863.21, 863.23; 55/16, 158; 436/116, 118, 167, 178, 902; 210/500.21

[56] References Cited

U.S. PATENT DOCUMENTS

| | | | |
|---|---|---|---|
| 3,667,918 | 6/1972 | Lyshkow | 422/86 X |
| 3,985,017 | 10/1976 | Goldsmith | 422/83 X |
| 4,348,358 | 9/1982 | McKee et al. | 422/87 X |
| 4,539,181 | 9/1985 | Westrup | 422/86 X |
| 4,692,309 | 9/1987 | Pannwitz | 422/88 X |
| 4,783,316 | 11/1988 | Pannwitz | 422/58 |

FOREIGN PATENT DOCUMENTS 3012380 10/1981 Fed. Rep. of Germany .

OTHER PUBLICATIONS

Article "Personal Sampler for $NO_x$," in the American Industrial Hygiene Association Journal.

Primary Examiner—Michael S. Marcus
Assistant Examiner—Rebekah A. Griffith
Attorney, Agent, or Firm—Walter Ottesen

[57] ABSTRACT

A diffusion sampler includes a vessel which has at least one inlet opening exposed to the gas to be investigated and which has a moderating zone. In its interior, the vessel has a collecting region provided with a collecting medium as well as a conversion region for converting the gas into substances which can be taken up by the collecting medium. The diffusion sample is improved in that its detection sensitivity is increased and that the collecting region as well as the converting region are provided with large areas in a manner adapted to the geometry of the vessel so that a smaller and more manipulable configuration is obtained. In addition, long-term dosimetry is made possible. For this purpose, the moderating zone is configured as a permeable barrier from which the converting region as well as the collecting region extend and determine the diffusion path in the entire interior of the vessel with each region being applied to a carrier.

12 Claims, 1 Drawing Sheet

DIFFUSION SAMPLER HAVING A CONVERSION ZONE

FIELD OF THE INVENTION

The invention relates to a diffusion sampler which includes a vessel having at least one inlet opening exposed to the gas to be investigated. A moderating zone is provided at the inlet opening. In its interior, the vessel includes a collecting region provided with a collecting medium as well as a conversion region for converting the gas into substances which can be taken up by the collecting medium.

BACKGROUND OF THE INVENTION

A diffusion sampler of the kind referred to above is disclosed in the technical journal entitled "American Industrial Hygiene Association Journal" (40) July 1979, pages 588 to 591.

The term diffusion sampler is understood to include pure collectors as well as indicating dosimeters.

The known diffusion sampler includes a tubular diffusion vessel which is suitable for collecting gaseous pollutants such as NO, $NO_2$ or also $NO_x$ and to make the same accessible for subsequent chemical analysis. The tubular vessel of the diffusion sampler is openable at one end and has a permeable lattice carrier at its end lying opposite the opening. The lattice carrier is provided with triethanolamine and is followed by a glass fiber disc impregnated with chromic acid. The $NO_x$ diffusing through the opening and a diffusion zone which follows the opening migrates to the base of the vessel where the $NO_2$ which is possibly present is held by the triethanolamine on the lattice carrier whereas the NO can diffuse through the lattice carrier and continue until it reaches the glass fiber disc whereat it is oxidized to $NO_2$ by the chromic acid impregnation and is likewise adsorbed on the triethanolamine layer of the lattice carrier.

The known diffusion sampler includes an air column which contributes a diffusion length through which the pollutants to be collected must pass. A significant disadvantage of this know diffusion sampler is seen in that a ratio between the vessel cross section and the height of the air column must be maintained at least 1 : 3 in order to obtain a reproducible diffusion. The extended length of the dosimeter vessel necessary for this reason makes it inconvenient to handle. In this connection, reference may be had to an article by S. R. Coleman in the technical journal entitled "American Industrial Hygiene Association Journal", 44 (9), page 632, (1983).

Furthermore, a length indicating dosimetry is not possible because the collecting tube would have to be extended still further and this would lead to an undesired enlargement of the diffusion vessel which would make the latter inconvenient to handle.

SUMMARY OF THE INVENTION

In view of the above, it is an object of the invention to improve a diffusion sampler of the kind referred to above such that its detection sensitivity is increased and so that the collecting region as well as the conversion region can be adapted to the geometry of the vessel and provide a large area so that a smaller and more manipulable configuration is obtained and so that a length indicating dosimetry is made possible.

The diffusion sampler according to the invention includes: a vessel defining an interior space and having at least one inlet opening exposed to the gas to be detected; permeable barrier means disposed in the inlet opening for defining a moderating zone through which the gas passes into the interior space; first and second carrier means extending into and through the interior space starting from the barrier means so as to conjointly define a diffusion path; collection means for taking up predetermined substances and being formed on the first carrier means; and, conversion means for converting the gas into the predetermined substances and being disposed on the second carrier means.

An advantage of the invention is seen in that a long diffusion length ahead of the conversion layer before the latter can be reached is eliminated. Conversion and collection now occur directly with the entry into the chamber defined by the vessel after the gas sample has passed through the diffusion barrier. As a diffusion barrier and moderating zone, it is adequate to provide a piece of filter paper closing the opening with the paper having a thickness of approximately 0.5 mm.

The carrier can utilize the entire inner space of the vessel. Respective carriers can be provided for the conversion region and the collecting region. On the other hand, a common carrier can be provided for both of these regions. For the substances to be collected as well as for the substances to be converted, only small diffusion paths have to be traversed because the carriers are arranged along the diffusion length and are parallel to each other. This achieves a rapid conversion and collection.

A further advantage of the invention is that also colorimetric detection surfaces and conversion surfaces can be utilized with the diffusion vessel being open at one end. In this context, the advancement of the coloration zone provides a time-calibrated measure for the collected dosage. The diffusion vessel can be used as a rapid gas dosimeter when both ends thereof are open.

The form of the carrier can be adapted to the form of the vessel. Accordingly, and in the context of a tubular vessel, it is conceivable to provide a central axially arranged circular rod. Also, centrally arranged struts can be mounted in the vessel which partition the diffusion tube into several longitudinally extending sections wherein respective collection and conversion regions are present.

In this way, very short diffusion paths for the conversion products are provided from the conversion surfaces to the collecting surfaces. This is especially the case when the corresponding surfaces are applied to porous or non-porous strips in the form of collecting layers or also in the form of indicating layers.

According to an embodiment of the invention, the collecting region is configured as a lining on the inner wall of the tubular vessel and the conversion region is provided on the surface of a carrier disposed inside of the tubular vessel. In the context, for example, of a wet chemical detection of substances taken-up on the collection surface, this configuration affords the advantage that the vessel only has to be rinsed after removal of the central carrier in order to obtain a quantitative detection. For the case that the collection surface comprises a colorimetric indicator, the coloration zone can be directly read off if the tube is transparent.

An equally advantageous embodiment is provided when the conversion region is defined by a lining on the inner surface of the tube and the collection region is provided on the surface of a carrier disposed within the tubular vessel.

In dependence upon the course of the conversion reaction, the quantity of the converted substances to be detected can be increased by the comparatively larger inner wall surface of the tubular vessel. At the same time, the quantitative detection of the collected substance can take place separately under suitable evaluation conditions after the central carrier has been removed from the tubular vessel.

It is advantageous to provide a closure at the inlet opening of the vessel which is permeable to the pollutants and which serves to hold back the converted products. This prevents the converted products from back-diffusing out of the inlet opening into the ambient especially at the beginning of the duration of collection. On the other hand, if the conversion products could diffuse back into the ambient then a subsequent evaluation would no longer be possible.

According to a feature of the invention, the closure is configured as a permeable membrane or also as a further collection layer in which the conversion products are collected and are likewise utilized for an evaluation.

For the purpose of detecting nitrogen oxides, the conversion region is advantageously made of chromium (VI-) oxide and the collection region is made of triethanolamine.

The embodiments of the diffusion sampler described above are not limited to only a diffusion vessel, for example, in the form of a glass tube; instead, other configurations are possible wherein a tube open at both ends is partitioned into two regions by an impermeable partition wall arranged within the tube. The two regions can be equipped with a conversion region and a collection region, respectively, and these regions can have different detection sensitivities.

On the other hand, a tubular vessel opened at one end and in the form of a dosimeter can have a permeable partition wall. The first region configured in this manner can contain an indicator layer in the vicinity of the inlet opening and be of higher detection sensitivity and the second region following the permeable partition wall can contain an indicator layer of lower detection sensitivity.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
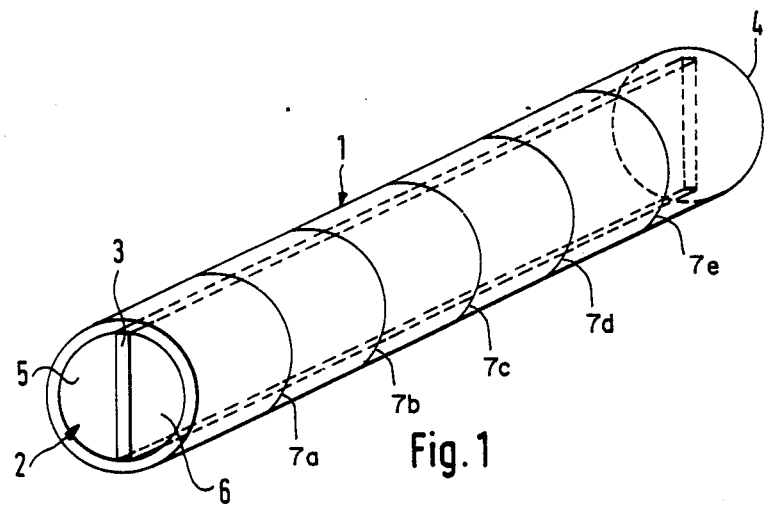
FIG. 1 is a perspective view of an embodiment of the diffusion sampler of the invention in the form of a dosimeter; and, FIG. 2 is a plan view, in section, of a further embodiment of the diffusion sampler according to another embodiment of the invention.

FIG. 1 shows a vessel of a gas dosimeter in the form of a tube 1 having a single inlet opening 2. The moderating zone in the form of a plug 10 (FIG. 2) has been deleted from FIG. 1 for clarity. A plate-shaped carrier 3 is seated in the interior of the tube 1 and extends up to the closed end 4 of the latter. The inner wall surface of the tube 1 is configured as a carrier for the collecting region 5. The conversion products formed at the conversion region 6 are collected at the collection region 5. The conversion region 6 is formed by both surfaces of the carrier 3.

For the situation wherein the collecting region 5 is a colorimetric indicator layer, a graded scale having scale markings 7a to 7e is provided on the outer surface of the tube 1 by means of which a direct reading of the dosage is possible as a consequence of the advance of the coloration zone in the collecting region 5.

Figure 2:
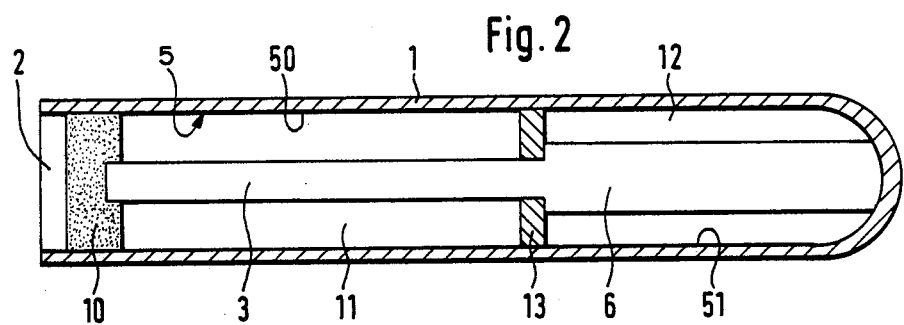

The embodiment shown in FIG. 2 shows the tube 1 in section wherein a permeable plug 10 closes the inlet opening 2. The plug 10 serves simultaneously as a holder for the rod-like axial carrier 3 having the conversion region 6 disposed on its entire surface. The inner surface of tube 1 is configured as the collection region 5 and is partitioned into component zones (50, 51).

The carrier 3 has a smaller surface in its first detection section 11 and a larger surface in the second detection section 12 thereof. Both detection sections (11, 12) are partitioned from each other by means of a permeable partition wall 13. In this way, the detection section 11 is suitable for detecting lower concentrations of pollutants and the detection section 12 is suitable for detecting higher pollutant concentrations, since the corresponding surfaces of the conversion region 6 on the carrier 3 are in the position to convert the correspondingly lesser or higher quantities of pollutants to be detected into conversion products so that these conversion products can be detected on the corresponding component zones (50, 51) of the collecting region 5.

It is understood that the foregoing description is that of the preferred embodiments of the invention and that various changes and modifications may be made thereto without departing from the spirit and scope of the invention as defined in the appended claims.

What is claimed is:

1. A diffusion sampler for detecting a gas, the diffusion sampler comprising:
   a vessel defining a longitudinal axis and an interior space and having at least one inlet opening exposed to the gas to be detected;
   permeable barrier means disposed in said inlet opening for defining a moderating zone through said gas passes into said interior space;
   first elongated carrier means extending along said axis and through said interior space starting from said barrier means;
   second elongated carrier means extending along and parallel to said axis and likewise extending through said interior space starting from said barrier means;
   said first and second carrier means conjointly defining a narrow gap transverse to said axis to provide a diffusion path therebetween which is arranged along the length of said vessel;
   conversion means disposed on first carrier means for converting said gas into predetermined substances which migrate across said gap; and,
   collection means for taking up said predetermined substances and being formed on said second carrier means to react with said predetermined substances to form a coloration indicaiton of the dosage of said gas.

2. The diffusion sampler of claim 1, said vessel having an interior surface defining said first carrier means and said second carrier means being a member seated in said vessel and having flat surface means formed thereon.

3. The diffusion sampler of claim 1, said vessel being a tubular vessel having an inner wall surface defining said first carrier means and said conversion means being formed as a lining on said inner all surface; and, said second carrier means being a member seated in said tubular vessel, said member having a surface for accommodating said collection means thereon.

4. The diffusion sampler of claim 1, said vessel being a tubular vessel having an inner wall surface defining said second carrier means and said collection means being formed as a lining on said inner wall surface; and, said first carrier means being a member seated in said tubular vessel, said member having a surface for accommodating said conversion means thereon.

5. The diffusion sampler of claim 1, wherein the gas to be detected is made up of nitrogen oxides and said conversion means being chromium (VI-) oxide and said collection means being triethanolamine.

6. The diffusion sampler of claim 1, said vessel having an interior surface defining said second carrier means and said first carrier means being a member seated in said vessel and having flat surface means formed thereon.

7. The diffusion sampler of claim 1, said barrier means comprising a closure seated in said inlet opening and being permeable to said gas while at the same time holding said converted substances in said vessel.

8. The diffusion sampler of claim 7, said closure being configured as a permeable membrane.

9. The diffusion sampler 7, said closure being configured as a collecting layer for taking up said substances.

10. The diffusion sampler of claim 1, said vessel including a partition wall for partitioning said interior space into two detection sections adapted for colorimetric dosimetry.

11. The diffusion sampler of claim 10, said partition wall being permeable to the gas to be detected.

12. The diffusion sampler of claim 10, said partition wall being impermeable to the gas to be detected.

* * * * *

UNITED STATES PATENT AND TRADEMARK OFFICE
CERTIFICATE OF CORRECTION

PATENT NO.  : 4,913,882

DATED       : April 3, 1990

INVENTOR(S) : Wolfgang May, Edgar Eickeler and Wolfgang Evers

It is certified that error appears in the above-identified patent and that said Letters Patent is hereby corrected as shown below:

In the ABSTRACT, line 7: delete "sample" and substitute -- sampler -- therefor.

In column 1, line 24: delete "$NO_2$" and substitute -- $NO_2$ -- therefor.

In column 4, line 58: delete "indicaiton" and substitute -- indication -- therefor.

In column 4, line 67: delete "all" and substitute -- wall -- therefor.

In column 6, line 9: insert -- of claim -- between "sampler" and "7,".

Signed and Sealed this

Ninth Day of July, 1991

Attest:

HARRY F. MANBECK, JR.

Attesting Officer

Commissioner of Patents and Trademarks